(12) United States Patent
Vilsmeier

(10) Patent No.: US 9,928,588 B2
(45) Date of Patent: Mar. 27, 2018

(54) INDICATION-DEPENDENT DISPLAY OF A MEDICAL IMAGE

(71) Applicant: Brainlab AG, Munich (DE)

(72) Inventor: Stefan Vilsmeier, Munich (DE)

(73) Assignee: Brainlab AG, Munich (DE)

(*) Notice: Subject to any disclaimer, the term of this patent is extended or adjusted under 35 U.S.C. 154(b) by 8 days.

(21) Appl. No.: 15/311,183

(22) PCT Filed: May 15, 2014

(86) PCT No.: PCT/EP2014/059969
§ 371 (c)(1),
(2) Date: Nov. 14, 2016

(87) PCT Pub. No.: WO2015/172833
PCT Pub. Date: Nov. 19, 2015

(65) Prior Publication Data
US 2017/0084028 A1    Mar. 23, 2017

(51) Int. Cl.
*G06K 9/00* (2006.01)
*G06T 7/00* (2017.01)
(Continued)

(52) U.S. Cl.
CPC ............ *G06T 7/0012* (2013.01); *G06T 11/60* (2013.01); *G06T 19/20* (2013.01); *G06T 2207/10004* (2013.01)

(58) Field of Classification Search
CPC .................................... G06T 7/00; A61B 5/00
(Continued)

(56) References Cited

U.S. PATENT DOCUMENTS 6,991,605 B2 * 1/2006 Lim .................... A61B 8/00
128/916

FOREIGN PATENT DOCUMENTS

WO    2007056601    5/2007

OTHER PUBLICATIONS

European Patent Office International Search Report for PCT/EP2014/059969 dated Mar. 13, 2015.
(Continued)

*Primary Examiner* — Abolfazl Tabatabai
(74) *Attorney, Agent, or Firm* — Middleton Reutlinger

(57) ABSTRACT

The present invention relates to a medical data processing method of determining an image of an anatomical structure of a patient's body, the method comprising the following steps which are constituted to be executed by a computer: a) acquiring (S1) GP atlas data describing an image-based model of at least part of a human body comprising the anatomical structure; b) acquiring (S1) patient medical image data describing a patient-specific medical image of the anatomical structure in the patient's body, wherein the patient medical image data comprises in particular three-dimensional image information c) determining (S2), based on the atlas data and the patient medical image data, atlas-patient transformation data describing a transformation between the image-based model and the anatomical structure in the patient's body; d) acquiring (S3, S4) medical indication data describing a medical indication which the anatomical structure is subject to; e) acquiring (S7) imaging parameter data describing at least one imaging parameter for generating, from the image-based model, an image of the anatomical structure in dependence on the medical indication data: f) determining (S8) indication image data describing an indication-specific image (1) of the anatomical structure in the patient, wherein the indication image data is determined (S8) based on the patient medical image data and the atlas-patient transformation data and the medical indication data and the imaging parameter data.

16 Claims, 2 Drawing Sheets

(51) Int. Cl.
 *G06T 19/20* (2011.01)
 *G06T 11/60* (2006.01)
 *A61B 5/103* (2006.01)

(58) Field of Classification Search
 USPC ....... 382/128, 129, 130, 131, 132, 133, 134; 600/300, 587
 See application file for complete search history.

(56) References Cited

OTHER PUBLICATIONS

Tschirley R, et al. "Patient-oriented segmentation and visualization of medical data", Proceedings of the Fifth Iasted International Conference Computer Graphics and Imaging Acta Press, pp. 214-219 Jan. 1, 2002.

* cited by examiner

INDICATION-DEPENDENT DISPLAY OF A MEDICAL IMAGE

The present invention is directed to a data processing method of determining an image of an anatomical structure of a patient's body in dependence on a medical indication.

When planning a medical procedure such as a therapeutic or surgical procedure, medical personnel such as a physician commonly wishes to have an image of the anatomical structure which shall undergo the medical procedure in order to have a visual impression of his working area. In many cases, the person planning the medical procedure wishes to have the anatomical structure presented in a view which is useful for conducting the planning. Such a view may for example be a standard view which in the medical arts is known to represent a view having the most useful information content for planning the procedure. For example, in the case of radiotherapy or radiosurgery on a tumour, the anatomical structure in which the tumour is located should be displayed in the image such that the tumour is visible. As another example, in the case of a fractured bone, the person planning the surgical procedure may wish to have the anatomical structure (embodied by the bone) presented in a manner which allows judging the location and type of the fracture. This manner of display is generally defined by standard views which radiologists or surgeons commonly use to judge specific types of fracture.

When assessing digital medical images in particular in three dimensions (such as computed x-ray tomographies or magnetic resonance tomographies), it may however be difficult for the person planning the procedure to manually adjust the manner in which the physical image is displayed so that the desired view can be achieved.

The invention is designed to be used with products offered by the applicant, Brainlab AG, such as Brainlab's Quentry® and/or Brainlab's Smartbrush®. Software: for Brainlab's elements such as Brainlab's ImageViewer and/or Brainlab's Smartbrush®. Smartbrush® is a software product for accelerated and straightforward volumetric tumour outlining in a medical image.

The algorithm employed by Smartbrush® allows for instant interactive volume creation in particular by automatically including regions in the image in a selection of three-dimensional image information (i.e. by automatically establishing a region of interest) which are adjacent to a two-dimensional path defined by movement of a user-operated pointing tool such as a mouse pointer. Thereby, a three-dimensional volume in a three-dimensional region of interest (representing e.g. a tumour) in a three-dimensional set of image data (e.g. CT data or MR data) can be efficiently created.

Quentry® is a platform for sharing image data (in particular medical image data) in a safe and secure manner, e.g. for collaboration between medical institutions. Quentry® includes an image viewer to which the present invention can in principal be applied.

Hardware devices offered by Brainlab AG to which the present invention may be applied (in particular, by adapting the software running on such hardware devices) to the BUZZ® centralized information for a digital operation room, the CURVE® information and control centre for image-guided surgery, and the KICK® platform for optical tracking.

A problem to be solved by the present invention is to provide a method of determining an image of an anatomical structure in dependence on the medical indication which the anatomical structure is subject to in particular such that a desired view of the anatomical structure can be reliably rendered.

This problem is solved by the subject-matter of any appended independent claim. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

EXEMPLARY SHORT DESCRIPTION OF THE PRESENT INVENTION

In the following, a short description of the specific features of the present invention is given which shall not be understood to limit the invention only to the features or a combination of the features described in this section.

The invention relates to a method of displaying an image comprising a perspective view of an anatomical structure (comprising at least one of soft tissue and hard tissue). The perspective is chosen in dependence on the relevant medical indication (i.e. pathologic state such as disease or injury) from which a real patient to be considered is suffering. Information about the pathologic state can be manually entered or automatically determined e.g. from comparing an image-based model of a corresponding healthy patient with a medical image taken from the real patient. A geometric parameter (also called imaging parameter) defining the perspective is defined relative to the model. Once a positional mapping between the model and the medical image has been established, it is possible to establish the spatial relationship between the geometric parameter and the medical image and to adjust a view onto medical image of the anatomical structure according to the geometric parameters. The geometric parameter differs for different indications and is entered into the data processing method in accordance with the indication entered or determined. The resulting view of the anatomical structure therefore is rendered in a perspective which is dependent on the indication. Since the geometric parameter may also define other quantities such as the extent of an anatomical region, not only the perspective but also other quantities defining the indication dependent view (such as e.g. the extent of the anatomical region to be displayed) may influence the view in an indication-dependent manner.

GENERAL DESCRIPTION OF THE PRESENT INVENTION

In this section, a description of the general, in particular preferred features, of the present invention is given.

In one aspect, the present invention is directed to a medical data processing method of determining an image of an anatomical structure of a patient's body. The anatomical structure is in particular the subject of a medical procedure, in particular it is the subject of computerised assessment without undergoing any surgical or therapeutic activity.

The method in accordance with the invention preferably comprises a step of acquiring atlas data describing (in particular defining) an image-based model of at least part of a human body. That part of a human body preferably comprises the anatomical structure (in particular, an anatomical structure corresponding in particular in its function to the anatomical structure of the patient which is subject to the medical indication). The anatomical structure may be any anatomical body part. For example, it may comprise, in particular consist of, soft tissue (such as brain tissue, lung tissue or skin) or hard tissue (such as a bone tissue or cartilage). As described further below in the section "Definitions", the atlas data is commonly generated on the basis of medical image data, the model of at least part of the human body therefore is image-based. The images used for generating preferably tomographic images which allow the model to be created such that is defined in three dimensions, i.e. is three-dimensional.

Preferably, patient medical image data is acquired which describes (in particular defines) a patient-specific medical image of the anatomical structure in the patient's body. The medical image has been generated preferably by imaging the real patient's body of which the anatomical structure is part and therefore it has been generated specifically for that patient (i.e. is patient-specific). The medical image comprises in particular three-dimensional image information and may be embodied by a tomography (such as a computed x-ray tomography, a magnetic resonance tomography or an ultrasound tomography). The medical image comprises image information representing an image of at least the anatomical structure.

Preferably, atlas-patient transformation data is determined based on the atlas data and the patient medical image data (in particular based on the image-based model and the patient-specific medical image). The atlas-patient transformation data describes (in particular defines) a transformation between the image-based model and the anatomical structure in the patient's body (in particular between the image-based model and the representation of the anatomical structure in the patient-specific medical image). In the framework of this disclosure, a transformation is understood to encompass (in particular, to be) a two- or three-dimensional coordinate mapping embodied by for example a linear multiplication matrix. Preferably, the transformation is affine. Preferably, the atlas-patient transformation data is determined by applying a fusion algorithm to the atlas data and the patient medical image data. For example, the image-based model is fused to the patient-specific medical image. This fusion algorithm may be an elastic fusion or an inelastic fusion. In other words, the image-based model is matched onto the patient-specific medical image. The resulting transformation therefore defines a coordinate mapping between positions in the image-based model and corresponding positions in the patient-specific medical image. The term "corresponding positions" in this context means in particular that image features in the image-based model are mapped onto corresponding image features in the patient-specific medical image. The positions do not have to be located at the same coordinates in both of the images. Rather, colour values (for example grey values or polychrome colour values) are compared in both images and a correspondence between images units (i.e. pixels or voxels) in both images is established by assessing the neighbourhood relationship of each image unit, in particular by finding image units in both images which have a similar distribution of colour values in their neighbourhood, in particular in neighbouring image units.

Preferably, medical indication data is acquired which describes (in particular defines) a medical indication which the anatomical structure is subject to. The term of medical indication encompasses in particular a pathologic state of the anatomical structure (such as a tumour disease or a fracture). Preferably, the method in accordance with the invention comprises a step of acquiring disease classification data. The disease classification data describes (in particular defines) pathologic states, in particular predetermined pathologic states. In particular, these pathologic states are pathologic states which the anatomical structure may be subject to. For example, the pathologic state may be a brain tumour and the disease classification data comprises information describing (in particular defining that the patient suffers from a brain disease and/or that the anatomical body part is the patient's head, i.e. the body region in which the tissue in which the pathologic state is present is located). The disease classification data may be acquired for example based on user input, for example by manually operating a graphical user interface (such as a dropdown menu) which contains a list of pathologic states. If the user selects one of those pathologic states to acquire the disease classification data by operating the graphical user interface, the method in accordance with the invention continues with acquiring the medical indication data on the basis of the pathologic state defined by the disease classification data. In the aforementioned example, the medical indication data may then be acquired such that it describes the medical indication.

Data describing (in particular defining) the envisages medical procedure for treating the pathologic state may also be acquired based on user input, for example by user selection of a preferred medical procedure usable for treating the pathologic state defined by the disease classification data. A list of useful medical procedures is preferably generated such that it is adapted to the relevant pathologic state. In particular, medical procedures which are not useful for treating the pathologic state are not defined by the medical indication data. This adaptation may be performed automatically, for example by extracting information from a database in which medical procedures are assigned to specific pathologic states.

Alternatively or additionally, disease classification data may be acquired by automatic pre-calculation. For example, the pathologic state may be determined by detection of abnormalities in the patient-specific medical image when comparing it to the image-based model, for example when determining the atlas-patient transformation data. For example, a pathologic state such as a tumour may not have any equivalent in the image-based model since the image-based model has been generated for a healthy patient. This will be reflected in the transformation resulting from fusing the atlas data to the patient medical image data (for example, by applying an elastic fusion algorithm which allows in particular for deformation of geometric relationships). On the basis of such information, the pathologic state present in the anatomical structure can be automatically determined or determined by offering the user a graphical user interface (such as a dropdown menu) in which potentially relevant pathologic states are listed and from which the user may choose one in order to define the pathologic state and thereby acquire (in particular enter) the disease classification data.

Preferably, imaging parameter data is acquired which describes (in particular defines) at least one imaging parameter for generating (in particular rendering) an image of the anatomical structure in dependence on the medical indication data. The imaging parameter describes (in particular defines) how an image of the anatomical structure should be generated from the image-based model in dependence on the medical indication, i.e. in order to visually assess the anatomical structure for the medical indication relevant for the patient. The at least one imaging parameter describes (in particular defines) at least one of the following:

- the position of the anatomical structure in the image-based model;
- the viewing direction in which the image of the anatomical structure in the image-based model is to be determined (in particular, the perspective from which the image is to be determined, i.e. from which the view of the anatomical structure should be generated; the term "perspective view" or "perspective" used in the context of the present invention comprises slice-view, multi-planar reconstruction, parallel or perspective view);
- a zoom factor and/or a zoom centre at which the image of the anatomical structure in the image-based model is to be displayed;
- at least one of anatomical landmarks and organs to be contained (in particular represented) in the image of the anatomical structure in the image-based model;
- the opacity/transparency values of specific image features in the aforementioned image;
- the anatomical extent of the aforementioned image (i.e. which anatomical structures should be represented by the image);
- in particular, the imaging parameter describes (more particularly, defines) a parameter such as a colour value (which may be a grey value or a polychrome colour value) for windowing an anatomical region of interest such that it is rendered in the image of the anatomical structure generated from the image-based model. The term of windowing encompasses determining the image based on surging the patient-specific medical image for at least one colour value representing the anatomical structure in the image-based model.

As described above, the imaging parameter describes (in particular defines) preferably positional information. The positional information may serve to define locations (such as the position of the anatomical structure in the image-based model) or directions (such as the viewing direction). The imaging parameter describes in particular the desired perspective from which the user wishes to view the anatomical structure in order to plan the envisaged medical procedure. The imaging parameter is preferably defined in a coordinate system used for defining positions in the image-based model, such as a patient coordinate system, view coordinate system, atlas coordinate system.

Preferably, indication image data is determined which describes (in particular defines) an indication-specific image of the anatomical structure in the patient. The indication image data is determined based on preferably the patient medical image data and the atlas-patient transformation data and the medical indication data and the imaging parameter data. As mentioned above, the positional information contained in the imaging parameter data is defined preferably in the coordinate system used for defining the image-based model. By applying the transformation described by the atlas-patient transformation data to the imaging parameter data (in particular, the positional information contained in the imaging parameter data), it is therefore possible to transform the positional information contained in the imaging parameter data into the coordinate system defining positions in the patient medical image data (in particular, in the patient-specific medical image). Thus, a predetermined (for example standard) view described by the imaging parameter data in the coordinate system of the image-based model can then be generated from the patient-specific medical image in order to give the user a visual impression of the anatomical structure of the specific patient from the desires perspective and comprising the desired information content (in particular representing the desired anatomical structures).

The atlas data may also serve as a separate basis (in addition to the atlas-patient transformation data) for determining the indication image data. For example, the atlas data may be used enhance the indication image data. In some, cases the patient medical image data may for example be of a low quality. This may for example occur if the patient medical image data was generated by computed x-ray tomography and the imaged body part such as the brain of the patient comprised a metal material—e.g. an electrode of a brain pacemaker or a metal implant which created artefacts in the patient-specific medical image. The atlas data comprises tissue class information which defines colour values (in particular greyscale values, but also polychrome values are potentially possible, for example after further processing of a greyscale image) associated with certain tissue types (e.g. soft tissue such as the tissue of an internal organ, skin or the brain; and hard tissue such as bony tissue or cartilage) in dependence on the medical imaging modality used for generating the medical image data from which the image-based model was generated. These colour values can be matched with the colour values (in particular greyscale values, but also polychrome values are potentially possible, for example after further processing of a greyscale image) of the patient-specific medical image. This matching can be used as basis for correcting errors in the patient-specific medical image such as e.g. the afore-mentioned artefacts in particular by replacing the colour values of the erroneous image units in the patient-specific-medical image with the colour values defined by the atlas data (in particular by the image-based model).

Preferably, display device data is acquired which describes (in particular defines) an imaging property of a display device on which the indication-specific image is to be displayed. Further preferably, the imaging parameter data (in particular the information describing (in particular defining) the imaging parameter, is acquired in dependence (i.e. based on) the display device data. In particular, the imaging parameter may be determined such that a performance characteristic (in particular, at least one of hardware characteristics and data processing capabilities) of a display device on which the indication-specific image shall be displayed is considered. For example, the manner in which the indication-specific image is displayed is adapted to the resolution achievable with the display device. The performance characteristic of the display device is described (in particular defined) by for example a value (in particular, numeric value or logic value) which is in the framework of this application called imaging property.

Preferably, display control data is determined which comprises information usable to control the display device to display the indication-specific image, in particular to generate the indication-specific image in or on the display device. The information contained in the display control data may for example define a manner which the image representation of the anatomical structure in the displayed indication-specific image shall be visually highlighted. For example, the image features of the indication-specific image which define the anatomical structure may be visually highlighted by rendering them in a colour differing the anatomical structure from surrounding image features which do not represent the anatomical structure. Alternatively or additionally, the image representation of the anatomical structure may be visually highlighted by a flashing effect or by labelling it for example with a human-readable text label.

Preferably, the method in accordance with the invention also comprises a step of acquiring medical procedure data describing (in particular defining) at least one of a specific medical procedure (in particular the medical procedure which the patient shall undergo in view of the medical indication described by the medical indication data) and a user (such as a medical technician or physician) who will view the indication-specific medical image. For example, the specific stage of the medical procedure may be the stage at which a dose distribution for radiotherapy or radiosurgery is planned or the stage at which the patient is placed in position for therapy. If the medical procedure is a surgical procedure such as an open operation, the specific stage of the medical procedure may be the stage at which the open surgery is being planned. The indication-specific image may then be rendered in a view (in particular, from a specific viewing direction, in particular perspective) which is commonly used for viewing the anatomical structure in the specific stage of the medical procedure or when viewed by that specific user. For example, a physician may be interested in a different view of the anatomical structure than a medical technician would be.

Preferably, the medical procedure data is acquired on the basis of the imaging parameter data. For example, the imaging parameter data may comprise information about a history of at least one imaging parameter which was previously used for that specific patient and for determining the indication image data. In particular, predetermined sequences of image parameters used for generating the indication-specific image of the anatomical structure for a specific patient may be used to uniquely determine the current stage of the medical procedure.

Preferably, entity navigation data is acquired which describes (in particular defines) the position of a navigated (in particular tracked) entity. The position of the entity is defined in particular relative to the position of the anatomical structure in the patient's body. The navigated entity is at least one of the human person (in particular a user such as any kind of medical personnel, for example a physician or a medical technician), the aforementioned display device and a medical instrument (for example, a catheter), an irradiation device for irradiating the anatomical structure with ionizing radiation (for example, a particle accelerator), and a surgical tool (for example, a scalpel). Being navigated in the context of this application means that the position of the navigated entity can be determined, for example by attaching a marker device in a predetermined (preferably known) spatial relationship (at least one of position and orientation) to the navigated entity and tracking the position of the marker device for example using an optical navigation system working on the basis of detecting reflection signals of electromagnetic radiation reflected from the surface of markers included in the marker device). The position of the anatomical structure in the patient's body can be known for example from the patient-specific medical image taken together with preferably information about the imaging geometry of a medical imaging device used to generate the patient medical image data and information about the position of the medical imaging device or of the patient's body in particular at the time at which the entity navigation data is acquired. The imaging parameter included in the imaging parameter data then preferably is specific for the spatial relationship of the navigated entity. In particular, the imaging parameter data is acquired based on the entity navigation data. For example, the imaging parameter may be acquired such that the viewing direction which it defines is dependent on the spatial relationship of the navigated entity, for example on the position of a catheter or the current viewing direction of the user. In this sense, the indication image data is then preferably determined further based on the entity navigation data.

Preferably, the patient medical image data comprises a plurality of image data sets which in particular have been generated with different imaging modalities. Each image data set is understood to define a self-contained medical image, in particular to represent one patient-specific medical image. According to one specific embodiment, the image data sets contained in the patient medical image data may have been generated with different imaging modalities. For example, one of the image data sets may define a patient-specific medical image which is a magnetic resonance tomography, and another one of the image data sets may define a patient-specific medical image which is a magnetic resonance tomography. Likewise, the indication image data may comprise a plurality of image data sets. Each one of these image data sets defines a self-contained indication-specific medical image, in particular each one of the image data sets included in the indication image data represents the one indication-specific medical image. The image data sets contained in the indication image data may according to a specific embodiment also have been generated with different imaging modalities. For example, one of the indication-specific medical images may be a computed x-ray tomography, and another one of the indication-specific medical images may be a magnetic resonance tomography. According to an advantageous embodiment, the image data sets contained in the indication image data have not been generated with an imaging modality which has not been used to generate at least one of the image data sets contained in the patient medical image data. In general, the indication-specific image described by the indication image data represents an image generated with the same imaging modality with which the patient medical image data serving as a basis for determining the indication image data has been generated.

If the indication image data contains a plurality of image data sets each describing one indication-specific medical image, the inventive method preferably comprises a step of determining display control data for controlling the aforementioned display device to display at least two of the indication-specific images simultaneously in an overlapping manner or simultaneously in a non-overlapping manner. Within the framework of this application, images are displayed in an overlapping manner if at least part of all the images concerned are displayed in the same region of the display surface (i.e. for example a set of pixels) of the display device. The term "being displayed simultaneously" in the framework of this application means in particular that the images are displayed such that a human viewer can recognize both images at the same point of time. If the images are displayed in a non-overlapping manner, they may be displayed on the same display device, or a plurality of display devices may be used and the images may be simultaneously displayed on different display devices. For example, each of the plurality of indication-specific images may be displayed on a separate display device.

The atlas data is in particular multi-modal atlas data describing an image-based model of at least part of the human body comprising the anatomical structure. Multi-modal atlas data is atlas data which contains image information about anatomical structures which has been generated by application of different imaging modalities. For example, the atlas data may contain an image-based model which has been generated by computed x-ray tomography and an image-based model which has been generated by magnetic resonance tomography. This allows receiving different image information for generating the image-based model. For example, magnetic resonance tomography allows to image body parts such as soft tissue which could not be imaged by application of computed x-ray tomography or which could be imaged by computed x-ray tomography only to a lesser extent or at lower quality. If for example the patient medical image data has been generated with magnetic resonance tomography, the indication-specific image could be enhanced by image information contained in the atlas data and generated by application of computed x-ray tomography. This would allow to for example have a precise rendering of hard tissue such as bones in the indication-specific image.

Preferably, acquiring the patient medical image data comprises generating the patient medical image data by imaging the anatomical structure with a medical imaging device based on the at least one imaging parameter. For example, the information which is contained in the imaging parameter data and defines the imaging parameter may be used as a basis for determining control signals for controlling the medical imaging device (such as a computed x-ray tomography scanner or a magnetic resonance tomography scanner or a conventional (in particular two-dimensional) x-ray imaging device or an ultrasound imaging device). In particular, the imaging geometry of the medical imaging device may be adjusted according to these control signals in order to generate the patient-specific medical image such that the imaging geometry corresponds to the information defined by the imaging parameter. For example, the medical imaging apparatus may be brought into a spatial relationship (in particular at least one of position and orientation) relative to the anatomical structure which resembles a perspective from the medical imaging device onto the anatomical structure which is defined by the imaging parameter.

In further aspects, the invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, in particular electrical, in particular technically generated) signal wave, in particular a digital signal wave, carrying information which represents the program, in particular the aforementioned program, which in particular comprises code means which are adapted to perform any or all of the method steps described herein.

In particular, the invention does not involve, comprise or encompass an invasive step which would represent a substantial physical interference with the body requiring professional medical expertise to be carried out and entailing a substantial health risk even when carried out with the required professional care and expertise. In particular, the invention does not involve, comprise or encompass any surgical or therapeutic activity. The invention is instead directed to a method usable for planning such a procedure. For this reason alone, no surgical or therapeutic activity and in particular no surgical or therapeutic step is necessitated or implied by carrying out the invention. Rather, the invention is preferably carried out before any such surgical or therapeutic activity or step is performed. Whether such surgical or therapeutic activity or step is then in fact executed, does not depend on whether the method in accordance with the invention is executed.

It is within the scope of the present invention to combine one or more features of one or more embodiments in order to form a new embodiment wherever this is technically expedient and/or feasible. Specifically, a feature of one embodiment which has the same or a similar function to another feature of another embodiment can be exchanged with said other feature, and a feature of one embodiment which adds an additional function to another embodiment can in particular be added to said other embodiment.

DEFINITIONS

In this section, definitions for specific terminology used in this disclosure are offered which also form part of the present disclosure.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit or CPU) which executes the computer program elements, and optionally a volatile memory (in particular a random access memory or RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which in particular comprises technical, in particular tangible components, in particular mechanical and/or electronic components. Any device mentioned as such in this document is a technical and in particular tangible device.

The method in accordance with the invention is in particular a data processing method. The data processing method is preferably performed using technical means, in particular a computer. The data processing method is preferably constituted to be executed by or on a computer and in particular is executed by or on the computer. In particular, all the steps or merely some of the steps (i.e. less than the total number of steps) of the method in accordance with the invention can be executed by a computer. The computer in particular comprises a processor and a memory in order to process the data, in particular electronically and/or optically. The calculating steps described are in particular performed by a computer. Determining steps or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term "computer" includes a cloud computer, in particular a cloud server. The term "cloud computer" includes a cloud computer system which in particular comprises a system of at least one cloud computer and in particular a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. In particular, the term "cloud" is used in this respect as a metaphor for the Internet (world wide web). In particular, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer in particular comprises interfaces in order to receive or output data and/or perform an analogue-to-digital conversion. The data are in particular data which represent physical properties and/or which are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals in particular represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, in particular handheld, device such as a smart phone or personal digital assistant or digital media player.

The expression "acquiring data" in particular encompasses (within the framework of a data processing method) the scenario in which the data are determined by the data processing method or program. Determining data in particular encompasses measuring physical quantities and transforming the measured values into data, in particular digital data, and/or computing the data by means of a computer and in particular within the framework of the method in accordance with the invention. The meaning of "acquiring data" also in particular encompasses the scenario in which the data are received or retrieved by the data processing method or program, for example from another program, a previous method step or a data storage medium, in particular for further processing by the data processing method or program. The expression "acquiring data" can therefore also for example mean waiting to receive data and/or receiving the data. The received data can for example be inputted via an interface. The expression "acquiring data" can also mean that the data processing method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step. In accordance with this additional step, the data are generated in order to be acquired. The data are in particular detected or captured (for example by an analytical device). Alternatively or additionally, the data are inputted in accordance with the additional step, for instance via interfaces. The data generated can in particular be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, in particular determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The atlas data preferably describes (in particular defines, more particularly represents and/or is) a general three-dimensional shape of the anatomical structure. The atlas data therefore represents an atlas of the anatomical body part. An atlas typically consists of a plurality of generic models of objects, wherein the generic models of the objects together form a complex structure. In particular, the atlas constitutes a statistical model of a patient's body (in particular, a part of the body) which has been generated from anatomic information gathered from a plurality of human bodies, in particular from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data.

The human bodies, the anatomy of which serves as an input for generating the atlas data, advantageously share a common feature such as at least one of gender, age, ethnicity, body measurements (e.g. size and/or mass) and pathologic state. The anatomic information describes in particular the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (so-called medical imaging modalities and/or radiological imaging methods) such as for instance computed tomography (CT) and cone beam computed tomography (CBCT, in particular volumetric CBCT), x-ray tomography, magnetic resonance tomography (MRT or MRI), conventional x-ray, sonography and/or ultrasound examinations, and positron emission tomography. The image data thus generated is also termed "medical imaging data". Analytical devices in particular are used to generate the image data in apparatus-based imaging methods. The imaging methods are in particular used for medical diagnostics, to analyse the anatomical body in order to generate images which are described by the image data. The imaging methods are also in particular used to detect pathological changes in the human body. However, some of the changes in the anatomical structure, in particular the pathological changes in the structures (tissue), may not be detectable and in particular may not be visible in the images generated by the imaging methods. A tumour represents an example of a change in an anatomical structure. If the tumour grows, it may then be said to represent an expanded anatomical structure. This expanded anatomical structure may not be detectable; in particular, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and in particular discernible in the image generated by the imaging method. In addition to these tumours, referred to as "enhancing" tumours, it is thought that approximately 10% of brain tumours are not discernible on a scan and are in particular not visible to a user looking at the images generated by the imaging method.

The information on the imaging geometry preferably comprises information which allows the analysis image (x-ray image) to be calculated, given a known relative position between the imaging geometry analysis apparatus and the analysis object (anatomical body part) to be analysed by x-ray radiation, if the analysis object which is to be analysed is known, wherein "known" means that the spatial geometry (size and shape) of the analysis object is known. This means in particular that three-dimensional, "spatially resolved" information concerning the interaction between the analysis object (anatomical body part) and the analysis radiation (x-ray radiation) is known, wherein "interaction" means for example that the analysis radiation is blocked or partially or completely allowed to pass by the analysis object. The location and in particular orientation of the imaging geometry is in particular defined by the position of the x-ray device, in particular by the position of the x-ray source and the x-ray detector and/or in particular by the position of the multiplicity (manifold) of x-ray beams which pass through the analysis object and are detected by the x-ray detector. The imaging geometry in particular describes the position (i.e. the location and in particular the orientation) and the shape (for example, a conical shape exhibiting a specific angle of inclination) of said multiplicity (manifold). The position can in particular be represented by the position of an x-ray beam which passes through the centre of said multiplicity or by the position of a geometric object (such as a truncated cone) which represents the multiplicity (manifold) of x-ray beams. Information concerning the above-mentioned interaction is preferably known in three dimensions, for example from a three-dimensional CT, and describes the interaction in a spatially resolved way for points and/or regions of the analysis object, in particular for all of the points and/or regions of the analysis object. Knowledge of the imaging geometry in particular allows the location of a source of the radiation (for example, an x-ray source) to be calculated relative to an image plane (for example, the plane of an x-ray detector). With respect to the connection between three-dimensional analysis objects and two-dimensional analysis images as defined by the imaging geometry, reference is made in particular to the following publications:

1. "An Efficient and Accurate Camera Calibration Technique for 3D Machine Vision", Roger Y. Tsai, Proceedings of the IEEE Conference on Computer Vision and Pattern Recognition. Miami Beach, Fla., 1986, pages 364-374
2. "A Versatile Camera Calibration Technique for High-Accuracy 3D Machine Vision Metrology Using Off-the-Shelf TV Cameras and Lenses", Roger Y. Tsai, IEEE Journal of Robotics and Automation, Volume RA-3, No. 4, August 1987, pages 323-344.
3. "Fluoroscopic X-ray Image Processing and Registration for Computer-Aided Orthopedic Surgery", Ziv Yaniv
4. EP 08 156 293.6
5. US 61/054,187

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change. In this application, the term "image morphing" is also used as an alternative to the term "elastic image fusion", but with the same meaning. Elastic fusion transformations (for example, elastic image fusion transformations) are in particular designed to enable a seamless transition from one dataset (for example a first dataset such as for example a first image) to another dataset (for example a second dataset such as for example a second image). The transformation is in particular designed such that one of the first and second datasets (images) is deformed, in particular in such a way that corresponding structures (in particular, corresponding image elements) are arranged at the same position as in the other of the first and second images. The deformed (transformed) image which is transformed from one of the first and second images is in particular as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are in particular vectors of a deformation field. These vectors are determined by the optimisation algorithm in such a way as to result in an optimum degree of similarity. Thus, the optimum degree of similarity represents a condition, in particular a constraint, for the optimisation algorithm. The bases of the vectors lie in particular at voxel positions of one of the first and second images which is to be transformed, and the tips of the vectors lie at the corresponding voxel positions in the transformed image. A plurality of these vectors are preferably provided, for instance more than twenty or a hundred or a thousand or ten thousand, etc. Preferably, there are (other) constraints on the transformation (deformation), in particular in order to avoid pathological deformations (for instance, all the voxels being shifted to the same position by the transformation). These constraints include in particular the constraint that the transformation is regular, which in particular means that a Jacobian determinant calculated from a matrix of the deformation field (in particular, the vector field) is larger than zero, and also the constraint that the transformed (deformed) image is not self-intersecting and in particular that the transformed (deformed) image does not comprise faults and/or ruptures. The constraints include in particular the constraint that if a regular grid is transformed simultaneously with the image and in a corresponding manner, the grid is not allowed to interfold at any of its locations. The optimising problem is in particular solved iteratively, in particular by means of an optimisation algorithm which is in particular a first-order optimisation algorithm, in particular a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there are a plurality of local optima, global algorithms such as simulated annealing or generic algorithms can be used. In the case of linear optimisation problems, the simplex method can for instance be used. In the steps of the optimisation algorithms, the voxels are in particular shifted by a magnitude in a direction such that the degree of similarity is increased. This magnitude is preferably less than a predefined limit, for instance less than one tenth or one hundredth or one thousandth of the diameter of the image, and in particular about equal to or less than the distance between neighbouring voxels. Large deformations can be implemented, in particular due to a high number of (iteration) steps. The determined elastic fusion transformation can in particular be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity. A measure of similarity can in particular be determined on the basis of a determined correlation between the first and second datasets.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is in particular part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is in particular known to a navigation system and is for example stored in a computer of the navigation system.

A "reference star" refers to a device with a number of markers, advantageously three markers, attached to it, wherein the markers are (in particular detachably) attached to the reference star such that they are stationary, thus providing a known (and advantageously fixed) position of the markers relative to each other. The position of the markers relative to each other can be individually different for each reference star used within the framework of a surgical navigation method, in order to enable a surgical navigation system to identify the corresponding reference star on the basis of the position of its markers relative to each other. It is therefore also then possible for the objects (for example, instruments and/or parts of a body) to which the reference star is attached to be identified and/or differentiated accordingly. In a surgical navigation method, the reference star serves to attach a plurality of markers to an object (for example, a bone or a medical instrument) in order to be able to detect the position of the object (i.e. its spatial location and/or alignment). Such a reference star in particular features a way of being attached to the object (for example, a clamp and/or a thread) and/or a holding element which ensures a distance between the markers and the object (in particular in order to assist the visibility of the markers to a marker detection device) and/or marker holders which are mechanically connected to the holding element and which the markers can be attached to.

A navigation system, in particular a medical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) in particular comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

A landmark is a defined element of an anatomical body part which is always identical or recurs with a high degree of similarity in the same anatomical body part of multiple patients. Typical landmarks are for example the epicondyles of a femoral bone or the tips of the transverse processes and/or dorsal process of a vertebra. The points (main points or auxiliary points) can represent such landmarks. A landmark which lies on (in particular on the surface of) a characteristic anatomical structure of the body part can also represent said structure. The landmark can represent the anatomical structure as a whole or only a point or part of it A landmark can also for example lie on the anatomical structure, which is in particular a prominent structure. An example of such an anatomical structure is the posterior aspect of the iliac crest. Another example of a landmark is one defined by the rim of the acetabulum, for instance by the centre of said rim. In another example, a landmark represents the bottom or deepest point of an acetabulum, which is derived from a multitude of detection points. Thus, one landmark can in particular represent a multitude of detection points. As mentioned above, a landmark can represent an anatomical characteristic which is defined on the basis of a characteristic structure of the body part. Additionally, a landmark can also represent an anatomical characteristic defined by a relative movement of two body parts, such as the rotational centre of the femur when moved relative to the acetabulum.

DESCRIPTION OF THE FIGURES

In the following, the invention is described with reference to the enclosed Figures which represent preferred embodiments of the invention. The scope of the invention is not however limited to the specific features disclosed in the Figures.

FIG. 1 shows the flow of steps of the method in accordance with the invention according to a preferred embodiment. The invention is not to be construed as being limited to the steps shown in FIG. 1.

In step S1, image data representing the patient medical image data is acquired along with the atlas data. In step S2, the atlas data is fused to the image data in order to determine the atlas-patient transformation data. On the basis of the thus-acquired patient image data and atlas data, the region of interest within the patient image data is detected in step S3 which encompasses in particular also the determination of the atlas-patient transformation data. Preferably, the detection of the region of interest of the patient image data is a body part detection, more preferably abnormality detection, i.e. detection of anatomic abnormalities such as a pathologic region (for example a tumour or a bone fracture) in the patient image data as a result of the fusion conducted in step S2. This involves in particular S4 which encompasses disease classification. As an optional step within the claimed method, the user manually defines more precisely the disease classification (S5).

In step S6, the view configuration is conducted using set of data obtained from steps S1 to S4, preferably steps S1 to S5. As a result of step 6, at least one view parameter (representing the imaging parameter included in the imaging parameter data) is acquired in step S7 such as at least one of view layout, field of view, image composition, overlays, windowing, anatomical structures.

In step S8, a viewer such as Brainlab's Quentry® image viewer and/or Brainlab's Smartbrush® determines the indication image data, in particular the indication-specific image, as at least one view to be displayed based on the results of step S7. As an optional step within the claimed method, the user in step S9 interacts with the viewer for inspecting displayed image data. The term "inspecting" used in this context encompasses image clipping, image zooming, image cropping, image rotating. Optional, steps S4 to S9 within the claimed method are repeated for precise displaying of the indication image data. As indicated by the arrows leading back from step S8 to the stage before execution of step S4, the indication-specific image generated in step S8 may serve as a basis for in particular visual inspection (e.g. in step S9) by e.g. medical personnel, who may choose to refine the disease classification of step S4 by in particular manual selection of a different pathologic state from e.g. a list provided before or within step S4.

Figure 1:
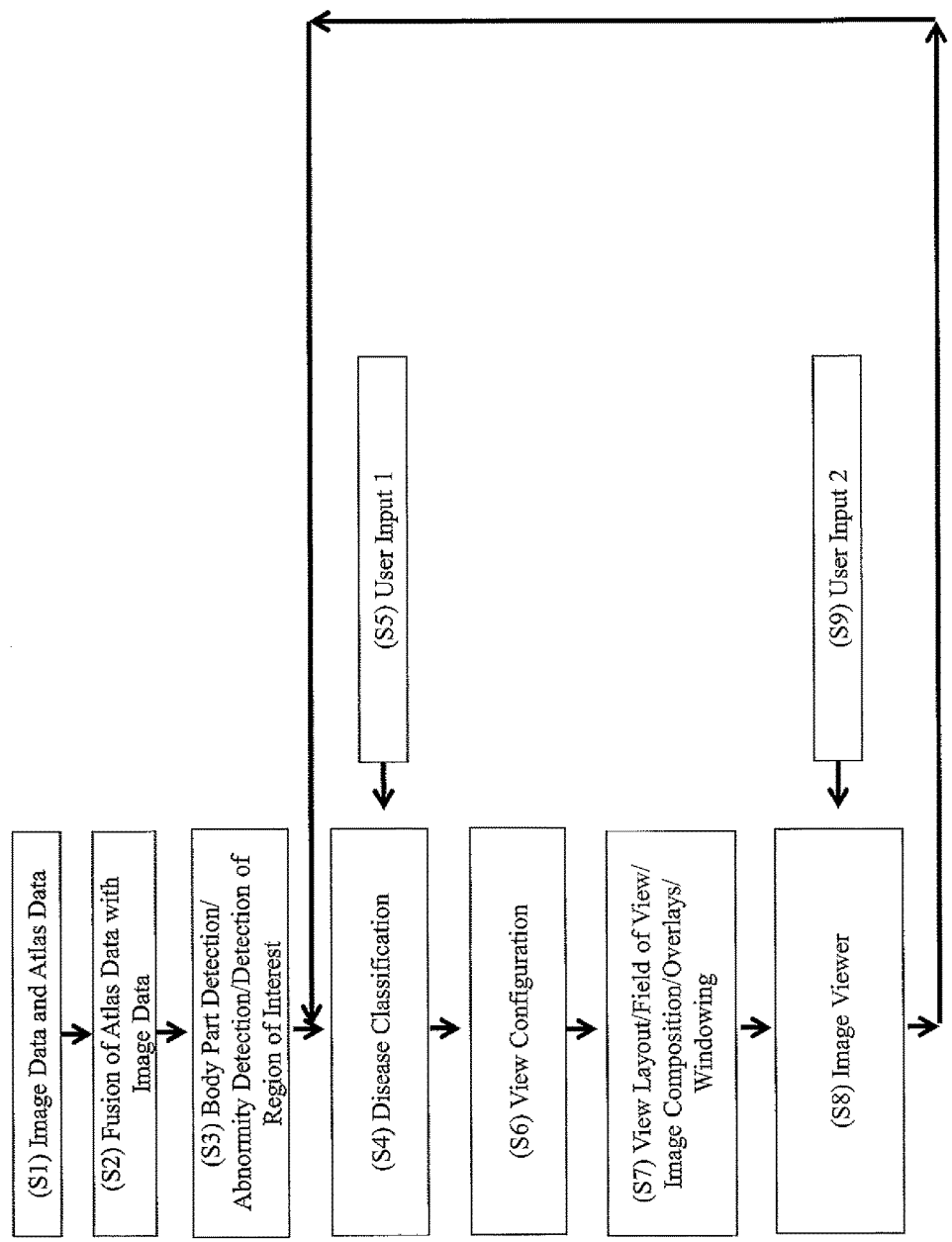
FIG. 1 is a flow diagram showing the steps of the method in accordance with the invention.
Figure 2:
FIG. 2 illustrates an indication-specific image of an anatomical structure embodied by the patient's skull and brain.

FIG. 2 illustrates an exemplary indication-specific image 1 of an anatomical structure comprising the patient's head and its constituents such as an in particular the brain 2. FIG. 2 illustrates that parts of the anatomical structure are represented by layers of graphical information. For example, the outer parts of the head such as the skin (shown as a white contour) are contained in one information layer, and the inner parts (such as the patient's brain and skull bone) are described by information contained in at least one other layer of graphical information (shown in darker grey shades). The indication-specific image is shown in a specific perspective 4 (indicated by the arrow on the left side of the indication-specific image 1) from the left of the patient's head which for planning the envisaged medical procedure has been determined to be an appropriate perspective. The perspective is further defined as "view up" which means that the top of the anatomical structure should be displayed at the top of the indication-specific image. A tumour 3 is delineated by a white contour as a region of interest.

The invention claimed is:

1. An image processing system, comprising:
   at least one display device;
   at least one processor;
   memory coupled to the at least one processor, wherein the memory stores instructions that, when executed by the at least one processor cause the at least one processor to:
   determine an image of an anatomical structure based on imaging performed by a medical imaging apparatus;
   and further including instructions to:
   a) acquire, at the at least one processor, atlas data describing an image-based model of at least part of a human body comprising the anatomical structure;
   b) acquire, at the at least one processor, patient medical image data describing a patient-specific medical image of the anatomical structure in the patient's body, wherein the patient medical image data comprises three-dimensional image information;
   c) determine, by the at least one processor and based on the atlas data and the patient medical image data, atlas-patient transformation data describing a transformation between the image-based model and the anatomical structure in the patient's body;
   d) acquire, at the at least one processor, medical indication data describing a medical indication which the anatomical structure is subject to;
   e) acquire, at the least one processor, imaging parameter data describing at least one imaging parameter for generating, from the image-based model, an image of the anatomical structure in dependence on the medical indication data;
   f) determine, by the at least one processor, indication image data describing an indication-specific image of the anatomical structure in the patient,
      wherein the indication image data is determined by the at least one processor, based on the patient medical image data and the atlas-patient transformation data and the medical indication data and the imaging parameter data;
      wherein the at least one computer is operably coupled to the at least one display device for displaying, on the at least one display device, the indication-specific image.

2. A computer-implemented image processing method of determining an image of an anatomical structure of a patient's body implemented by at least one processor, comprising:
   a) acquiring, at the least one processor, atlas data describing an image-based model of at least part of a human body comprising the anatomical structure;
   b) acquiring, at the at least one processor, patient medical image data describing a patient-specific medical image of the anatomical structure in the patient's body, wherein the patient medical image data comprises three-dimensional image information;
   c) determining, by the at least one processor, based on the atlas data and the patient medical image data, atlas-patient transformation data describing a transformation between the image-based model and the anatomical structure in the patient's body;
   d) acquiring, at the at least one processor, medical indication data describing a medical indication which the anatomical structure is subject to;
   e) acquiring, at the at least one processor, imaging parameter data describing at least one imaging parameter for generating, from the image-based model, an image of the anatomical structure in dependence on the medical indication data;
   f) determining, by the at least one processor, indication image data describing an indication-specific image of the anatomical structure in the patient, wherein the indication image data is determined by the at least one processor, based on the patient medical image data and the atlas-patient transformation data and the medical indication data and the imaging parameter data.

3. The method according to claim 2, wherein the medical indication data is acquired, at the at least one processor, in dependence on the atlas-patient-transformation data or based on user input.

4. The method according to claim 2, further comprising:
   acquiring, at the at least one processor, display device data describing an imaging property of a display device on which the indication-specific image is to be displayed;
   wherein the imaging parameter data is acquired at the at least one processor, in dependence on the display device data.

5. The method according to claim 2, further comprising:
   determining, by the at least one processor, display control data for controlling a display device to display the indication-specific image;
   displaying the indication-specific image based on the display control data;
   visually highlighting the image representation of the anatomical structure in the displayed indication-specific image.

6. The method according to claim 2, comprising
   acquiring, at the at least one processor, medical procedure data describing at least one of a specific stage of a medical procedure and a user who will view the indication-specific medical image,
   wherein the indication image data is determined, by the at least one processor, in dependence on the medical procedure data.

7. The method according to claim 6, wherein the medical procedure data is acquired, at the at least one processor, on the basis of the imaging parameter data.

8. The method according to claim 7, wherein the medical procedure data is acquired, at the at least one processor, based on a history of at least one previously imaging parameter used for determining the indication image data.

9. The method according to claim 2, comprising:
   acquiring, at the at least one processor, entity navigation data describing the spatial relationship of a navigated entity relative to the position of the anatomical structure in the patient's body,
   wherein the at least one imaging parameter is acquired based on the spatial relationship of the navigated entity, and
   wherein the indication image data is determined, by the at least one processor, based on the entity navigation data.

10. The method according to claim 9, wherein the navigated entity is at least one of a user, a display device on which the indication-specific image is to be displayed, and a medical instrument.

11. The method according to claim 2, wherein the patient medical image data and the indication image data each comprise a plurality of image data sets which have been generated with different imaging modalities, each image data set contained in the patient medical image data representing one patient-specific medical image and each image data set contained in the indication medical image data representing one indication-specific medical image, the method further comprising a step of:

determining, by the at least one processor, display control data for controlling a display device to display at least two of the indication-specific images simultaneously in an overlapping or simultaneously in a non-overlapping manner.

12. The method according to claim 11, wherein the indication-specific images are displayed in a non-overlapping manner on a same display device or on different display devices.

13. The method according to claim 12, wherein the display device is included in a computer monitor or in a handheld digital device, a personal digital assistant or in an augmented reality device.

14. The method according to claim 2, wherein the at least one imaging parameter describes at least one of the position of the anatomical structure in the image-based model, the viewing direction in perspective from, which the image of the anatomical structure in the image-based model is to be determined, a zoom factor and/or zoom center at which the image of the anatomical structure in the image-based model is to be displayed, at least one of anatomical landmarks and organs to be contained in the aforementioned image, the opacity/transparency of image features in the aforementioned image and the anatomical extent of the aforementioned image for windowing an anatomical region of interest such that it is rendered in the aforementioned image based on searching the patient-specific medical image for at least one color value representing the anatomical structure in the image-based model.

15. The method according to claim 2, wherein acquiring the patient medical image data comprises generating the patient medical image data by imaging the anatomical structure with a medical imaging device based on the at least one imaging parameter.

16. A non-transitory computer-readable program storage medium storing a program which, when executed by at least one processor of at least one computer or loaded into at least one memory of at least one computer, causes the computer to execute a computer-implemented image processing method of determining an image of an anatomical structure of a patient's body, the method comprising executing, by at least one processor of at least one computer steps of:

a) acquiring, at the least one processor, atlas data describing an image-based model of at least part of a human body comprising the anatomical structure;

b) acquiring, at the at least one processor, patient medical image data describing a patient-specific medical image of the anatomical structure in the patient's body, wherein the patient medical image data comprises three-dimensional image information;

c) determining, by the at least one processor, based on the atlas data and the patient medical image data, atlas-patient transformation data describing a transformation between the image-based model and the anatomical structure in the patient's body;

d) acquiring, at the at least one processor, medical indication data describing a medical indication which the anatomical structure is subject to;

e) acquiring, at the at least one processor, imaging parameter data describing at least one imaging parameter for generating, from the image-based model, an image of the anatomical structure in dependence on the medical indication data;

f) determining, by the at least one processor, indication image data describing an indication-specific image of the anatomical structure in the patient, wherein the indication image data is determined by the at least one processor, based on the patient medical image data and the atlas-patient transformation data and the medical indication data and the imaging parameter data.

\* \* \* \* \*